United States Patent
Spriggs

Patent Number: 5,954,500
Date of Patent: Sep. 21, 1999

[54] GUARD FOR TEETH WITH BRACES

[76] Inventor: Stephen Todd Spriggs, 4827 Thunderbird Dr., #91, Boulder, Colo. 80303

[21] Appl. No.: 09/160,456

[22] Filed: Sep. 24, 1998

[51] Int. Cl.⁶ ............................................. A61C 5/14
[52] U.S. Cl. .................................. 433/6; 128/861; 433/22
[58] Field of Search ...................... 433/2, 6, 22; 128/861, 128/862

[56] References Cited

U.S. PATENT DOCUMENTS

| | | | |
|---|---|---|---|
| 1,934,688 | 11/1933 | Ackerman | 128/861 |
| 2,257,709 | 9/1941 | Anderson | 128/861 |
| 3,314,423 | 4/1967 | Boatwright et al. | 128/861 |
| 4,512,740 | 4/1985 | Kurz | 433/6 |
| 4,904,188 | 2/1990 | Baurmash | 128/861 |
| 5,035,613 | 7/1991 | Breads et al. | 433/6 |
| 5,037,296 | 8/1991 | Karwoski | 433/22 |
| 5,055,039 | 10/1991 | Abbatte et al. | 433/6 |

*Primary Examiner*—Todd E. Manahan
*Attorney, Agent, or Firm*—G. F. Gallinger

[57] ABSTRACT

A guard for teeth having braces having lateral connectors therebetween comprises: an upper shield having an exterior wall adapted to encircle a person's teeth in their upper jaw; and, a lower shield having an exterior wall adapted to encircle a person's teeth in their lower jaw, said said shields extending downwardly generally the length of the teeth, and then across the biting surface of the teeth, and then partially along an inward length of the teeth. The shields have spaced hooks for positioning which are adapted to extend inwardly to the teeth and along an inward side portion of the lateral connectors between the braces. The hooks are adapted to extend from a top portion of the upper shield over and behind the connectors so that the shield will stay positioned on the teeth when a user opens their mouth and from a bottom portion of the lower sheild under and behind the connectors.

5 Claims, 1 Drawing Sheet

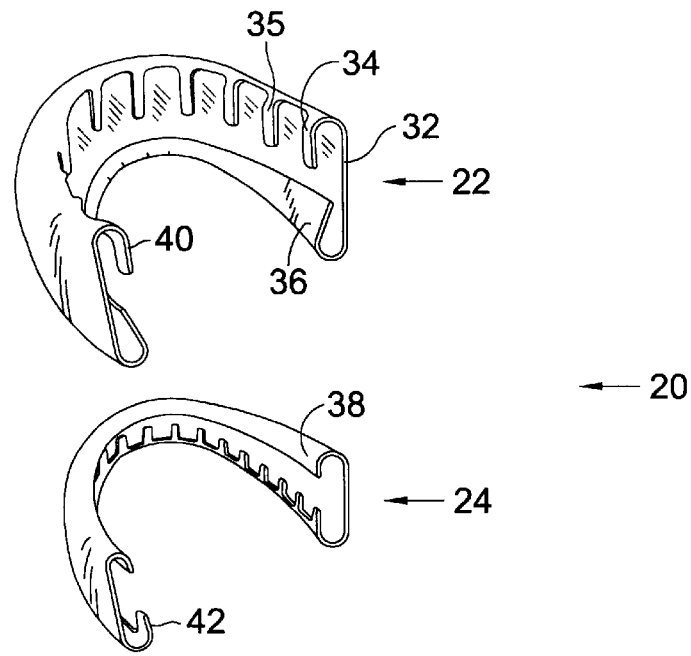
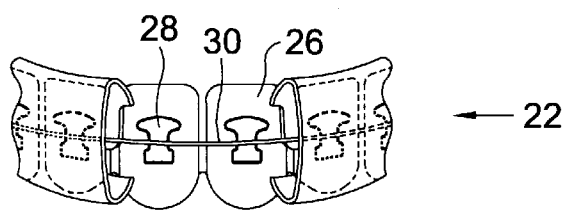
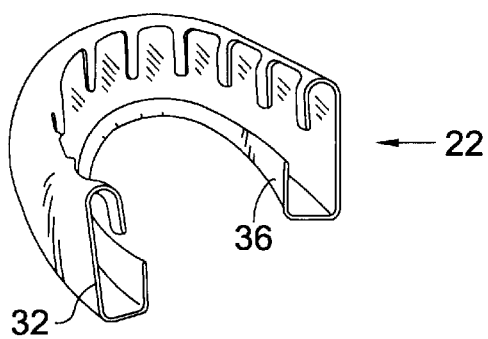

GUARD FOR TEETH WITH BRACES

FIELD OF INVENTION

This invention relates to teeth braces installed by orthodontists to straighten teeth. It also relates to athletic teeth guards used to protect teeth in sports. More particularly it relates to a teeth guard which may be worn with orthodontic braces to protect teeth, braces, and lips from injury.

BACKGROUND OF THE INVENTION

A substantial number of young people wear orthodontic braces to straighten their teeth and correct their bite. These braces usually comprise of a lateral wire which encircles the teeth between braces (or anchoring pads) adhered to outer side portions of the teeth. When a young person participates in sports where blows are occasionally received to the face, these braces may be problematic. A conventional teeth guard cannot be worn with braces. If a person wearing orthodontic braces receives even a mild blow, say from a basketball, their lips frequently catch in the braces and may be severely torn.

With a forceful blow, in addition to the lips being torn, the braces may be disrupted. There is of particular need for a teeth guard which may be worn with braces. This teeth guard would not only protect the teeth, but additionally protect the braces, and the lips, which are particularly prone to injury when braces are worn.

OBJECTS AND STATEMENT OF INVENTION

It is an object of this invention to disclose a teeth guard which may be worn with orthodontic braces. It is an object of this invention to disclose a teeth guard which will afford protection to teeth, braces, and lips in the event of a blow. It is a further object of this invention to disclose a teeth guard which may be secured and maintained in position by the wire or lateral connectors on orthodontic braces so that the wearer may talk and communicate while wearing the braces. It is yet a further object of this invention to disclose a guard which may be worn while eating to prevent food from lodging between orthodontic braces and the teeth. It is yet a further object of this invention to disclose a guard which improves the asthetic appearance of braces while being worn. It is a final object of this invention to disclose a teeth guard which is inconspicuous and convenient to wear.

One aspect of this invention provides for a guard for teeth having braces having lateral connectors there between comprising: an upper shield having an exterior wall adapted to encircle a person's teeth in their upper jaw, said upper shield extending downwardly generally the length of the teeth, and then across the biting surface of the teeth, and then partially along an inward length of the teeth; and, a lower shield having an exterior wall adapted to encircle a person's teeth in their lower jaw, said lower shield extending downwardly generally the length of the teeth, and then across the biting surface of the teeth, and then partially along an inward length of the teeth. Each shield has spaced hook and positioning means adapted to extend inwardly to the teeth and along an inward side portion of the lateral connectors between the braces so that the shield will stay positioned on the teeth when a user opens their mouth. The hook and positioning means are adapted to extend from a top portion of the upper shield over and behind the connectors and extend from a bottom portion of the lower brace under and behind the connectors.

Another aspect of this invention provides for a guard as above wherein said hook and positioning means is formed first by rolling the upper portion of the inner wall on the upper shield in and downwardly, and the bottom portion of the exterior wall on the lower shield in and upwardly, and then cutting the rolled portions so that hooks are formed therein.

Various other objects, advantages and features of novelty which characterize this invention are pointed out with particularity in the claims which form part of this disclosure. For a better understanding of the invention, its operating advantages, and the specific objects attained by its users, reference should be made to the accompanying drawings and description, in which preferred embodiments of the invention are illustrated.

FIGURES OF THE INVENTION

The invention will be better understood and objects other than those set forth will become apparent to those skilled in the art when consideration is given to the following detailed description thereof. Such description makes reference to the annexed drawings wherein:

FIG. 1 is a perspective view of the teeth guard which comprises an upper shield and a lower shield.

FIG. 2 is a broken away view of an upper shield of the guard for teeth with braces shown on a person's upper teeth.

FIG. 3 is a perspective view of an alternate embodiment of an upper shield for teeth with braces.

The following is a discussion and description of the preferred specific embodiments of this invention, such being made with reference to the drawings, wherein the same reference numerals are used to indicate the same or similar parts and/or structure. It should be noted that such discussion and description is not meant to unduly limit the scope of the invention.

DESCRIPTION OF THE INVENTION

Turning now to the drawings and more particularly to FIG. 2 we have a broken away view of an upper shield 22 of a guard 20 for teeth with braces. The teeth 26 have braces 28 having lateral connectors 30 therebetween. Usually these lateral connectors 28 are wires.

FIG. 1 is a perspective view of the teeth guard 20 which comprises an upper shield 22 and a lower shield 24. The upper shield 22 has an exterior wall 32 adapted to encircle a person's teeth 26 in their upper jaw (not shown). The upper shield 22 extends downwardly generally the length of the teeth 26, and then across the biting surface of the teeth 26, and then partially along an inward length of the teeth 26. Similarly the lower shield 24 has an exterior wall 32 adapted to encircle a person's teeth 26 in their lower jaw (not shown). The lower shield 24 extends downwardly generally the length of the teeth 26, and then across the biting surface of the teeth 26, and then partially along an inward length of the teeth 26. Each shield 22, 24 has spaced hook and positioning means 34 adapted to extend inwardly to the teeth and along an inward side portion of the lateral connectors 30 between the braces 28 so that the shield will stay positioned on the teeth 26 when a user opens their mouth (not shown). The hook and positioning means 34 are adapted to extend from a top portion of the upper shield 22 over and behind the connectors 30 and from a bottom portion of the lower sheild 24 under and behind the connectors 30.

Most preferably the hook and positioning means 34 comprises a hook 35 extending in and downwardly from an upper portion of the exterior wall 32 on the upper shield 22, and a hook 35 extending in and upwardly from a bottom portion of the exterior wall 32 on the lower shield 24. When the shields 22, 24 are positioned on the teeth 26, these hooks 35 then extend in the direction which the adjacent teeth 26 have grown.

In the embodiment of the guard 20 shown in FIG. 1 the bottom portion 36 of the exterior wall 32 on the upper shield 22 is rolled in and upwardly and the top portion 38 of the exterior wall 32 on the lower shield 24 is rolled in and downwardly. These inwardly rolled portions 36, 38 add to shock absorption when the guard 20 receives a blow.

FIG. 3 is a perspective view of an alternate embodiment of a guard 20 for teeth 26 with braces 28. In FIG. 3 only the upper sheild 22 is shown. The lower shield 24, which is not shown in this embodiment, has a similar design. In this embodiment the bottom portion of the exterior wall 32 on the upper shield 22 and the top portion of the exterior wall on the lower shield (neither shown) are rolled inwardly across the cutting side portion of the teeth 26 and then in and along an interior side portion of the teeth 26 generally in an opposite direction to which the teeth 26 have grown. In as much as the front teeth 26 are not as thick as the teeth 26 corresponding to the sides of the guard 20, the guard is narrower on its front portion. The embodiment shown in FIG. 3 is stronger and preferred in sports where more severe blows may be possible.

Most preferably the shields 22, 24 are generally made from a tooth colored molded plastic which is sufficiently soft to be cut for individual adaption. It is contemplated that the guards 20 will be made in three sizes to accomodate different sized jaws. The number of hooks 35 on a shield 22, 24 may be substantially in excess of the number of teeth 26 in a jaw so that only the hooks 35 which correspond to the spaces in between teeth 26 will be used, while the others will be removed. In use the shields 22, 24 are first hooked around the front teeth 26 and thereafter hooked along the teeth 26, working towards the back of the mouth.

While the invention has been described with preferred specific embodiments thereof, it will be understood that this description is intended to illustrate and not to limit the scope of the invention. The optimal dimensional relationships for all parts of the invention are to include all variations in size, materials, shape, form, function, assembly, and operation, which are deemed readily apparent and obvious to one skilled in the art. All equivalent relationships to those illustrated in the drawings, and described in the specification, are intended to be encompassed in this invention. What is desired to be protected is defined by the following claims.

I claim:

1. A guard for teeth having braces having lateral connectors therebetween comprising:

an upper shield having an exterior wall adapted to encircle a person's teeth in their upper jaw, said upper shield extending downwardly generally the length of the teeth, and then across the biting surface of the teeth, and then partially along an inward length of the teeth; and, a lower shield having an exterior wall adapted to encircle a person's teeth in their lower jaw, said lower shield extending downwardly generally the length of the teeth, and then across the biting surface of the teeth, and then partially along an inward length of the teeth;

each shield having spaced hook and positioning means adapted to extend inwardly to the teeth and along an inward side portion of the lateral connectors between the braces so that the shield will stay positioned on the teeth when a user opens their mouth;

said hook and positioning means adapted to extend from a top portion of the upper shield over and behind the connectors and from a bottom portion of the lower shield under and behind the connectors.

2. A guard as in claim 1 wherein said hook and positioning means comprises a hook extending in and downwardly from an upper portion of the exterior wall on the upper shield, and a hook extending in and upwardly from a bottom portion of the exterior wall on the lower shield.

3. A guard has in claim 1 wherein the shields are generally made from molded plastic.

4. A guard as in claim 3 wherein the shields are generally tooth colored.

5. A guard has in claim 4 which is made from a sufficiently soft plastic to be cut for individual adaption.

\* \* \* \* \*